United States Patent
Meyer et al.

(10) Patent No.: US 11,463,522 B1
(45) Date of Patent: Oct. 4, 2022

(54) SYSTEM AND METHOD FOR EFFICIENTLY TRANSMITTING SIGNALS WITH REPEATING STRUCTURES

(71) Applicant: UIPCO, LLC, San Antonio, TX (US)

(72) Inventors: Gregory Brian Meyer, San Antonio, TX (US); Mark Anthony Lopez, Helotes, TX (US); Ravi Durairaj, San Antonio, TX (US); Nolan Serrao, Plano, TX (US); Victor Kwak, Frisco, TX (US); Ryan Thomas Russell, The Colony, TX (US); Christopher Russell, The Colony, TX (US); Ruthie D. Lyle, Durham, NC (US)

(73) Assignee: United Services Automobile Association (USAA), San Antonio, TX (US)

( * ) Notice: Subject to any disclaimer, the term of this patent is extended or adjusted under 35 U.S.C. 154(b) by 0 days.

(21) Appl. No.: 16/942,830

(22) Filed: Jul. 30, 2020

Related U.S. Application Data

(60) Provisional application No. 62/880,709, filed on Jul. 31, 2019.

(51) Int. Cl.
| | |
|---|---|
| *H04L 67/12* | (2022.01) |
| *H04W 84/18* | (2009.01) |
| *H04W 4/38* | (2018.01) |
| *A61B 5/026* | (2006.01) |

(52) U.S. Cl.
CPC .......... *H04L 67/12* (2013.01); *A61B 5/0261* (2013.01); *H04W 4/38* (2018.02); *H04W 84/18* (2013.01)

(58) Field of Classification Search
CPC ........ H04L 67/12; H04W 4/38; H04W 84/18; A61B 5/0261
See application file for complete search history.

(56) References Cited

U.S. PATENT DOCUMENTS

| | | | |
|---|---|---|---|
| 10,873,791 B1 * | 12/2020 | Carl | H03M 7/6047 |
| 2014/0073958 A1 * | 3/2014 | Rodriguez-Llorente | A61B 5/7221 600/479 |
| 2017/0344706 A1 * | 11/2017 | Torres | G16Z 99/00 |
| 2021/0169426 A1 * | 6/2021 | Garudadri | G01R 13/0272 |

FOREIGN PATENT DOCUMENTS

| | | | |
|---|---|---|---|
| CN | 102697520 A | * | 10/2012 |
| KR | 20150012094 A | * | 2/2015 |

* cited by examiner

*Primary Examiner* — Austin J Moreau
(74) *Attorney, Agent, or Firm* — Plumsea Law Group, LLC

(57) ABSTRACT

A system and method for efficiently transmitting signals from a sensing device to a remote device are disclosed. The sensing device includes at least one sensor for sensing information. The sensed information could be associated with heart activity. The sensing device smooths the sensed signal and then calculates the difference between the smoothed sensed signal and a locally stored baseline signal to determine a differential signal, which can be transmitted as a smaller packet of data than the full sensed signal. The remote device receives information associated with the differential signal and uses a local copy of the baseline signal to reconstruct the original smoothed sensed signal.

20 Claims, 9 Drawing Sheets

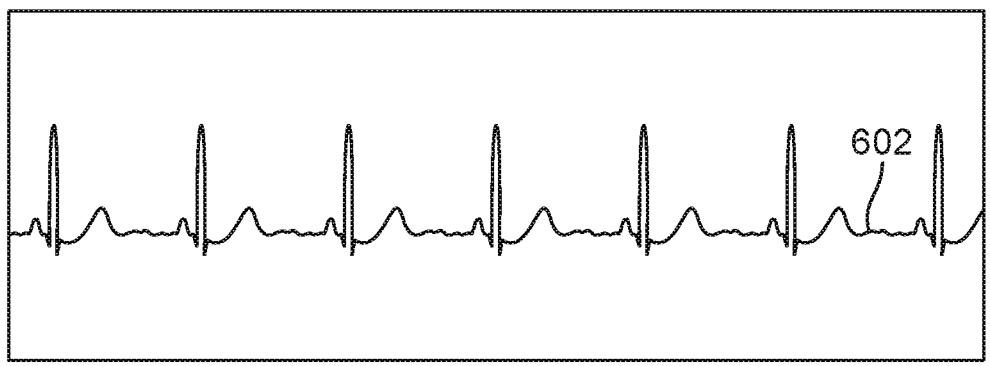
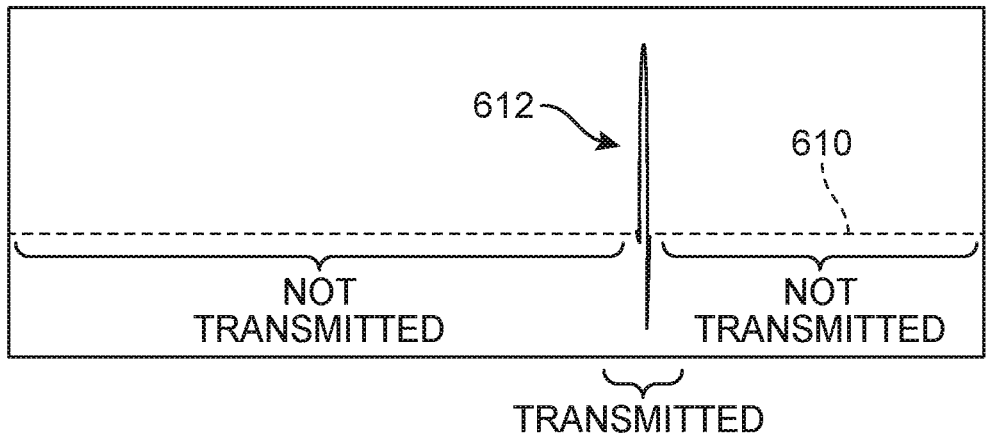
FIG. 6

SYSTEM AND METHOD FOR EFFICIENTLY TRANSMITTING SIGNALS WITH REPEATING STRUCTURES

CROSS-REFERENCE TO RELATED APPLICATIONS

This application claims the benefit of Provisional Patent Application No. 62/880,709 filed Mar. 31, 2019, and titled "System and Method for Efficiently Transmitting Signals with Repeating Structures," which is incorporated by reference herein in its entirety.

TECHNICAL FIELD

The present disclosure generally relates to data transmission, and in particular to a system and method for transmitting data efficiently.

BACKGROUND

Many wearable devices now exist that can detect biometric data, including data such as heartbeats, steps taken, perspiration levels, as well as other kinds of information. These devices are often small and have limited computing resources to analyze and apply the sensed data. Analysis and long-term storage of the data is usually accomplished by a server.

Users of these devices may find themselves in locations with limited connectivity. Additionally, the devices may have low-power requirements. When the sensed data is real-time, or otherwise nearly continuous, it may be especially difficult to transmit all the data to a server for further processing and storage.

There is a need in the art for a system and method that addresses the shortcomings discussed above.

SUMMARY

In one aspect, a method of improving the efficiency of transmitting sensed information from a sensing device to a receiving device includes steps of sensing a signal with a sensor, retrieving a baseline signal, transforming the sensed signal into a smoothed sensed signal, determining differences between the smoothed sensed signal and the baseline signal, and sending at least some of the differences between the smoothed sensed signal and the baseline signal to the receiving device.

In another aspect, a method of reconstructing a sensed signal received from a sensing device includes a step of receiving data, where the data comprising differences between a sensed signal and a first baseline signal. The method also includes a step of retrieving a second baseline signal, where the second baseline signal is substantially similar to the first baseline signal. The method also includes a step of reconstructing a new signal from the baseline signal and the data.

In another aspect, a communication system for efficiently transmitting signals includes a sensing device. The sensing device further includes a sensor, a first baseline signal stored in a first memory, and a signal processing unit. The communication system also includes a remote device that further includes a second baseline signal stored in a second memory and a signal processing unit. The second baseline signal is substantially identical to the first baseline signal. The sensing device is configured to detect a sensed signal using the sensor, transform the sensed signal into a smoothed sensed signal, determine differences between the smoothed sensed signal and the first baseline signal, and transmit the differences between the smoothed sensed signal and the first baseline signal to the analyzing system. The remote device is configured to receive the differences between the smoothed sensed signal and the first baseline signal transmitted by the sensing device, and use the second baseline signal and the differences between the smoothed sensed signal and the first baseline signal to reconstruct the smoothed sensed signal.

Other systems, methods, features, and advantages of the disclosure will be, or will become, apparent to one of ordinary skill in the art upon examination of the following figures and detailed description. It is intended that all such additional systems, methods, features, and advantages be included within this description and this summary, be within the scope of the disclosure, and be protected by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like reference numerals designate corresponding parts throughout the different views.

FIG. 6 is a schematic view of a step of determining the difference between a smoothed sensed signal and a baseline signal;

DESCRIPTION OF THE EMBODIMENTS

A system and method for efficiently transmitting signals from a sensing device to a remote device are disclosed, which overcome the limitations addressed above. Specifically, the system and method allow signals with regular or repeated structure to be sent in an efficient manner. That is, the amount of data that must be transmitted between two devices is significantly less than the amount of data required to encode the original signal. Moreover, this process differs from other source coding methods by leveraging repetition/patterns in the signal (encoded in a baseline signal) that are known a priori. With knowledge of the typical, or average, behavior of the signal, only differences between the sensed signal and a baseline signal must be sent. Upon receiving the differences in the signals, a receiving device may reconstruct the sensed signal using the transmitted differences along with a local copy of the baseline signal. Not only is the amount of data transferred reduced because much of the signal is encoded in the baseline signal that already exists at the sending and receiving devices, but the present system and method also help minimize power consumption by the transmitting device (the sensing device). For example, if a real-time continuous signal needs to be transmitted from a sensing device to a receiving device, the sensing device can transmit only at times when the signal differs substantially from the baseline signal.

Figure 1:
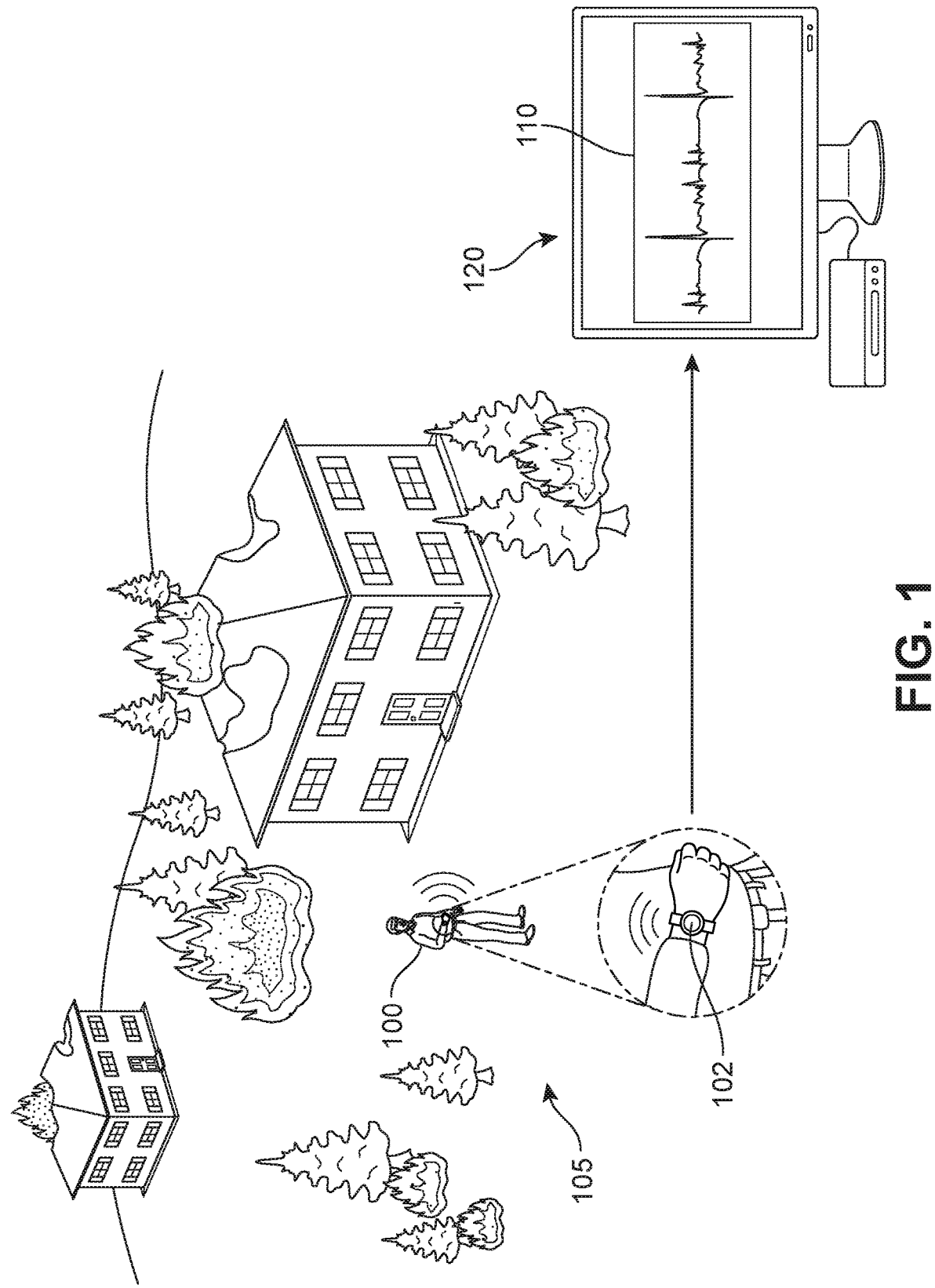
FIG. 1 is a schematic view of a user deployed in a disaster area whose heart rate is being monitored at a separate location, according to an embodiment.

FIG. 1 is a schematic view of an exemplary situation where signals may need to be transmitted from a device in one location to a server or other system at a second location. In the example shown in FIG. 1, a user 100 is an emergency responder who has been deployed to a disaster area 105. That is, an area that has recently experienced a flood, fire, hurricane, tornado, or other disaster. In this case, disaster area 105 is an area experiencing wild fires. User 100 has a wearable device 102 that has sensors that are able to continuously monitor an electrical signal associated with the user's heart function. This sensed electrical signal 110 can then be sent to a remote server 120 where it can be monitored for signs of stress that might indicate that user 100 is in trouble and needs to be evacuated or otherwise provided with additional support.

In disasters, communication infrastructure (such as cell towers) may be damaged which leads to limited connectivity between user 100 and remote server 120. Because of both this limited connectivity, and the power constraints of many wearable devices (such as device 102), any signals transmitted between device 102 and server 120 should be as efficient as possible. That is, the amount of data transmitted should be as small as possible due to possible latency issues on the network. Also, the amount of time the device spends transmitting should be limited to help conserve power.

Figure 2:
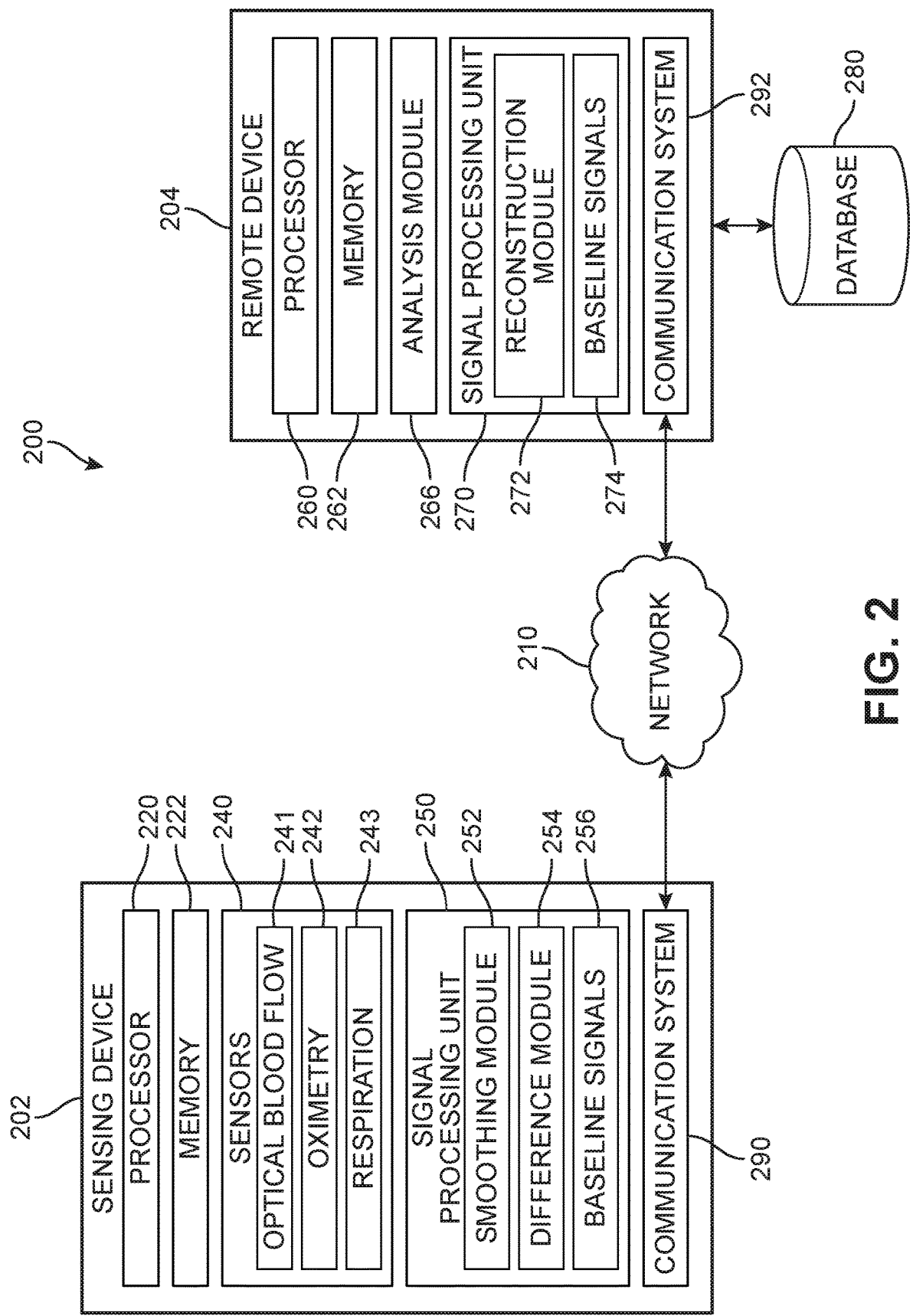
FIG. 2 is a schematic view of a communication system, according to an embodiment.

FIG. 2 is a schematic view of a communication system 200 that facilitates efficient communication for some types of signals. Specifically, system 200 facilitates efficient communication for signals that have predictable baselines, or predictable repeated structure. One example of an electrical signal with predictable repeated structure includes electrical signals associated with heart function, such as the sensed electrical signal 110 in FIG. 1. This type of signal can be generated by placing one or more electrodes on a person's skin. If the signal is generated using a sufficient number of electrodes in particular places, the plot of the signal is often referred to as an electrocardiogram (ECG). These signals may be decomposed into normal patterns of heart activity. For example, the portion of a signal associated with each heart beat is understood to include a P wave, a QRS complex, a T wave and a U wave. Based on patterns of these entities, heart rate and physiological heart rhythms can be identified and monitored for anomalies such as bradycardia (below normal heart rate), tachycardia (above normal heart rate), and cardiac arrhythmias (irregular rhythms). Communication system 200 could also be used to transmit other sensed signals associated with a user and/or the user's environment. For example, continuously monitored temperature, perspiration, breathing, and other vital indicators or behaviors could be used provided the sensing device is equipped with suitable sensors to detect the associated signals.

In other embodiments, communication system 200 could be used to efficiently transmit other kinds of sensed signals with regular or repeating baseline patterns. For example, after an earthquake, signals from one or more seismometers could be transmitted from sensing devices in the earthquake area to a remote device over a network.

Communication system 200 includes a sensing device 202 and a remote device 204 that is disposed at a different location from sensing device 202. In particular, it may be assumed that remote device 204 is sufficiently far enough from sensing device 202 that signal transmissions can be degraded by intermediate communication infrastructure. Sensing device 202 could include any device capable of sensing information. In some embodiments, sensing device 202 could be a mobile device, such as a mobile phone or tablet. In other embodiments, sensing device 202 could be a wearable device, such as a smartwatch or fitness tracker. Remote device 204 could be any device with sufficient computing resources to receive data from sensing device 202. In some cases, remote device 204 could be a server. In the exemplary embodiment, remote device 204 also includes provisions for storing and monitoring/analyzing the received signals. However, in other embodiments, a remote device could simply be a receiving device and could pass received signals to yet other systems or devices for analysis and/or storage.

Sensing device 202 may include a processor 220 and memory 222. Memory 222 may comprise a non-transitory computer readable medium. Instructions stored within memory 222 may be executed by the one or more processors 220.

Sensing device 202 may also include one or more sensors 240. The type of sensors used may vary from one embodiment to another and may depend on the type of sensing device. In an embodiment where sensing device 202 is a smartwatch or other wearable, sensors 240 could include heart rate monitors (such as an optical blood flow sensor 241 that can be used to infer heart rate), an oximetry sensor 242 to measure blood oxygen, and a respiration sensor 243. In some cases, a respiration sensor could be a radar-based sensor capable of detecting very small movements, such as the rise and fall of a user's chest. Other sensors could include a skin conductance sensor and a skin temperature sensor. Still other sensors could include sensors found in many mobile devices, such as a gyroscope, an accelerometer, a GPS receiver, as well as other suitable sensors.

Sensing device 202 may further include a signal processing unit 250. Signal processing unit 250 includes provisions for processing information retrieved from the one or more sensors 240. Specifically, signal processing unit 250 includes a smoothing module 252, a difference module 254 and one or more baseline signals 256 that may be stored in memory. As described in further detail below, signal management unit 250 may transform an incoming signal from sensors 240 using these modules and baseline signals.

Smoothing module 252 may include algorithms for smoothing a sensed signal, which may contain a lot of noise. Smoothing module 252 could implement a variety of different smooth algorithms. In some cases, smoothing module 252 could implement an unweighted sliding-average smoothing algorithm. In other cases, smoothing module 252 could implement the Savitzky-Golay algorithm, which is another well-known smoothing algorithm based on least-squares fitting.

Difference module 254 may include algorithms for calculating the difference between two signals. Any known algorithms for computing the differences between two signals could be implemented by difference module 254. If the signals have a time lag, techniques such as cross-correlation could be used to determine the time lag so that the difference can be computed. Additionally, difference module 254 could implement other provisions to normalize the signals or otherwise adjust the signals in a way that makes a direct subtraction or other comparison more suitable.

Baseline signals 256 may comprise one or more predicted or expected signals. These signals may be specific to a particular context. For example, as described in further detail below, electrical signals of heartbeat activity may be associated with an expected or predicted baseline signal for normal heart function.

Remote device 204 may include a processor 260 and memory 262. Memory 262 may comprise a non-transitory computer readable medium. Instructions stored within memory 262 may be executed by the one or more processors 260.

Remote device 204 may also include an analysis module 266. Analysis module 266 may include one or more software applications or algorithms for analyzing signals received from sensing device 202. The type of analysis used may depend on the context. In an embodiment where an electrical signal associated with heart activity is received, the analysis module could comprise a tool for monitoring the heart activity, detecting abnormal heart activity, and providing notifications when abnormal activity is detected.

Remote device 204 also includes a signal processing unit 270. Signal processing unit 270 includes provisions for processing received signals. Specifically, signal processing unit 270 includes a reconstruction module 272 and one or more baseline signals 274 that can be used to reconstruct a signal, as described in further detail below.

In some cases, remote device 204 also communicates with a separate database 280. Database 280 may be used to store baseline signals, software applications or other data. Additionally, signals processed by remote device 204 may also be stored in database 280.

Sensing device 202 may communicate with remote device 204 over a network 210. Network 210 could be any wide area network (WAN), local area network (LAN), and/or personal area network (PAN). In some embodiments, network 210 could comprise a cellular network that connects sensing device 202 and remote device 204 over the internet.

To facilitate communication, each of sensing device 202 and remote device 204 may include a communication system. Specifically, sensing device 202 includes a first communication system 290 and remote device 204 includes a second communication system 292. Each communication system may include radios or other provisions for communicating using one or more communication methods. For example, each communication system could include a Wi-Fi radio, a Bluetooth radio, and/or a cellular network radio.

In some embodiments, two or more sensing devices could communicate directly with one another over a mesh network. In some cases, the mesh network could be a Bluetooth based mesh network. In such cases, data could be transferred between the devices over the mesh network so that devices with sufficient connectivity to remote device 204 over a wide area network could transmit and receive data on behalf of one or more of the sensing devices. Such a configuration may allow devices with insufficient connectivity to transmit signal information to other devices that have sufficient connectivity to ensure the data can be received at remote device 204.

Figure 3:
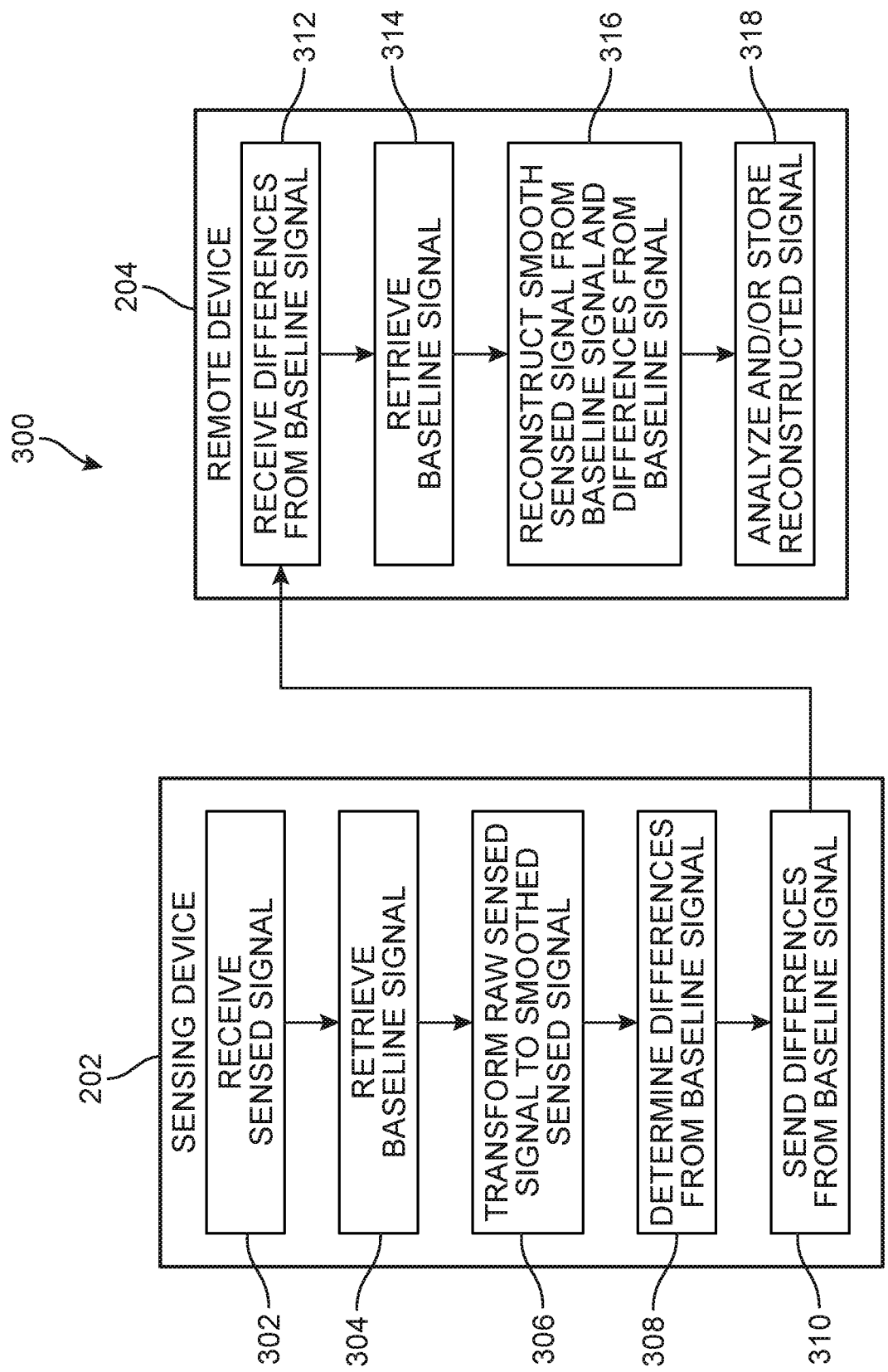
FIG. 3 is a schematic view of a process associated with the communication system of FIG. 2, according to an embodiment.

FIG. 3 is a schematic view of a process of sending a signal in an efficient manner between a sensing device and a remote device. As shown in FIG. 3, some of the steps may be performed by sensing device 202, while other steps may be performed by remote device 204.

Starting in step 302, sensing device 202 may receive a sensed signal. Specifically, signal processing unit 250 may receive information from one or more of sensors 240. For example, if device 202 is a smart watch with a sensor capable of detecting heart activity, signal processing unit 250 may receive information corresponding to a user's heart activity.

Figure 4:
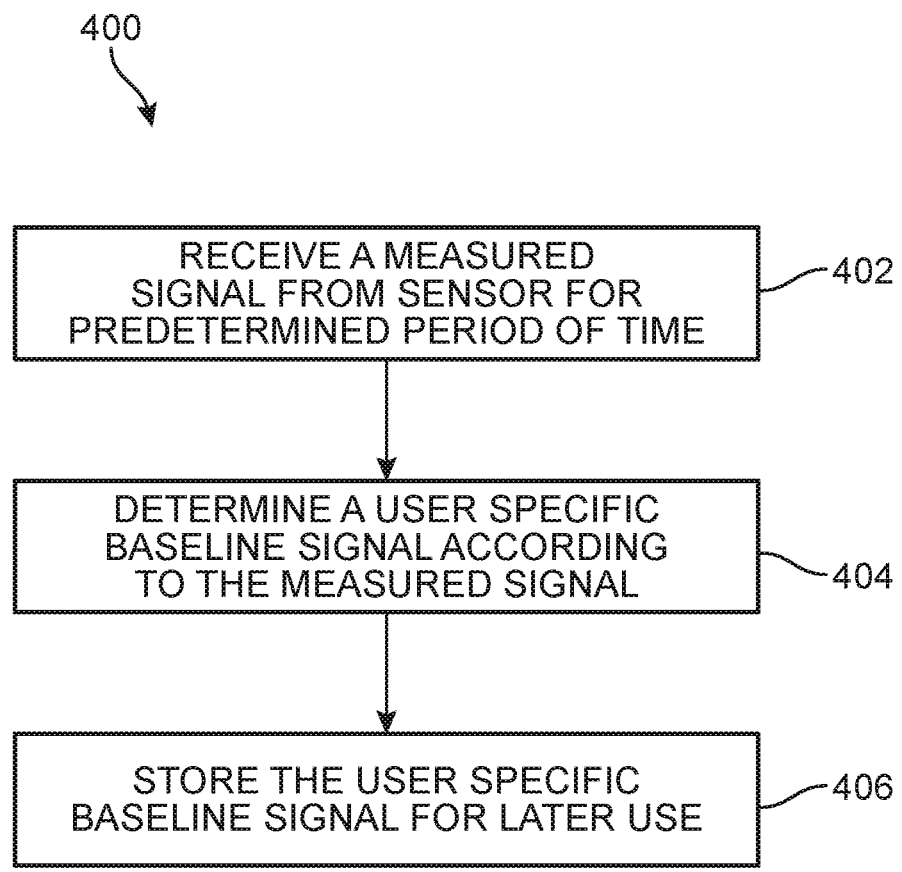
FIG. 4 is a schematic view of a process for determining a user specific baseline, according to an embodiment.

Next, in step 304, sensing device 202 may retrieve a baseline signal. If the sensed signal is associated with heart activity, the baseline signal may be a baseline heart activity signal. In some embodiments, the retrieved baseline signal may be an average baseline signal for a given population. In other embodiments, the retrieved baseline signal could be specific to a particular user. For example, the process shown in FIG. 4 depicts how a user specific baseline can be determined. In particular, in a first step 402, a system can receive a measured signal from a sensor for a predetermined period of time. The period of time may depend on the context. For heart rate activity, a baseline could be established by monitoring heart activity over a few minutes or hours. Next, in step 404, a system may determine a user specific baseline signal according to the measured signal. To do this, the system may identify repeating patterns in the data and determine an average signal over time (or over a given interval). Finally, in step 406, the system may store the user specific baseline signal for later use. For example, the user specific baseline signal may be stored on both a sensing device (such as sensing device 202) and a remote device (such as remote device 204).

Figure 5:
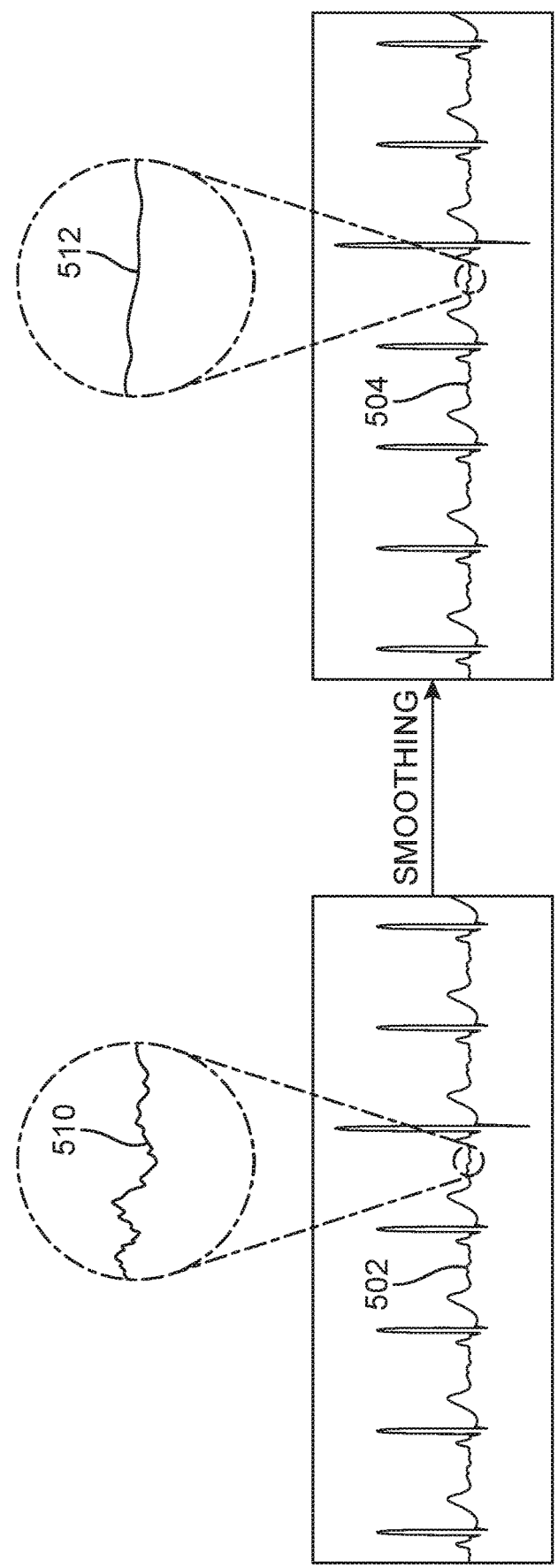
FIG. 5 is a schematic view of a step of smoothing a sensed signal, according to an embodiment.

Referring back to the process in FIG. 3, once the baseline signal has been retrieved, sensing device 202 may transform the raw sensed signal to a smoothed sensed signal in step 306. Specifically, the signal can be smoothed using smoothing module 252 to remove noise and/or variations in the signal below a particular threshold. FIG. 5 illustrates a schematic view comparing a pre-processed (that is, raw) signal 502 and a smoothed signal 504. The global shape of these signals is substantially similar, however raw signal 502 includes significantly more noise in the signal as shown in the comparison between enlarged segment 510 of raw signal 502 and enlarged segment 512 of smoothed signal 504.

Next, in step 308, sensing device 204 determines the differences between the retrieved baseline signal and the raw sensed signal. This process can be seen schematically in FIG. 6. Here, a baseline signal 602 is subtracted from smoothed signal 504 to produce a differential signal 610. Differential signal 610 has a value of 0 at all locations except an anomalous segment 612. This anomalous segment 612 corresponds to a segment 520 of smoothed signal 504 where the heart activity fluctuates substantially from the baseline, or expected, activity. Such a fluctuation could indicate an abnormal heart beat, for example.

In step 310, sensing device 202 sends only the differences between the smoothed sensed signal and the baseline signal to remote device 204. Because the values of the differential signal are substantially equal to 0 at all but a small number of locations, this results in a significantly more efficient transmission of data than if the entire sensed signal (or smoothed sensed signal) were transmitted. In particular, sensing device 302 need not send data for the portions of the signal that are substantially close to 0. Instead, as indicated in FIG. 6, sensing device 202 may only send data associated with the anomalous segment 612. With this configuration, the transmission time can be substantially reduced compared to transmitting the full signal. This is because sensing device 202 need only transmit data during brief intervals when the signal differs substantially from the baseline signal. This has the effect of reducing the power consumed by using one or more radios of sensing device 202.

In some embodiments, difference data may only be sent when the values are outside a particular threshold range. In some cases, the absolute value of the threshold range may be determined according to the values of the raw signals and/or baseline signals. As an example, if the raw and baseline signals are normalized to have maximum values of 1, the threshold range could be selected to be −0.1 to 0.1 (that is, plus or minus 10 percent of the maximum value). In other words, if the absolute value of the difference between the raw (or smoothed) signal and the baseline signal is less than 0.1, the algorithm may treat them as being substantially 0 and the values need not be transmitted. Of course, these particular values are only intended to be illustrative and the threshold values used in other embodiments may be selected to balance data transmission efficiency with accuracy of the reconstructed signal.

In step 312, remote device 204 receives the differences in the two signals (that is, the nonzero segments of the differential signal). Next, remote device 204 retrieves a local copy of the baseline signal in step 314. This baseline signal may be identical to the baseline signal stored on sensing device 202 and used to determine the differential signal.

Figure 7:
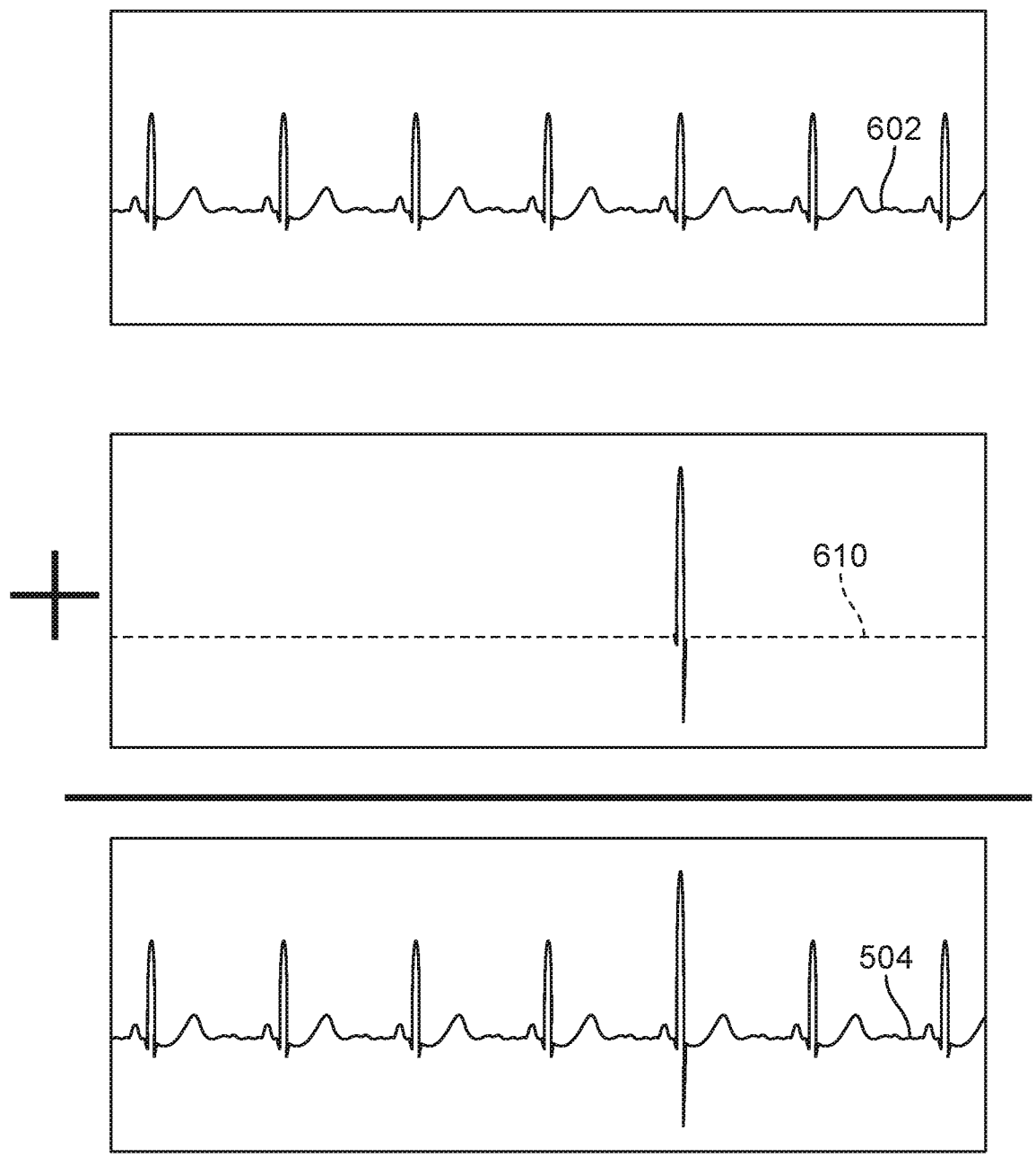
FIG. 7 is a schematic view of a step of reconstructing a smoothed sensed signal from a baseline signal and transmitted data.

In step 316, remote device 204 uses the baseline signal and the received differential signal to reconstruct the smoothed sensed signal that was initially created by sensing device 202. This process can be seen schematically in FIG. 7. In this case, the baseline signal 602 (stored locally) is added to the differential signal 610 (received from the sensing device) to reconstruct the smoothed sensed signal 504.

After reconstructing the smoothed sensed signal 504, remote device 204 may analyze and/or store the reconstructed signal in step 318. For example, in the exemplary situation shown in FIG. 1, remote device 204 could be used to monitor the heart activity of user 100 and provide alerts to another party if any anomalies have been detected that would indicate that user 100 is stressed or should otherwise be evacuated from the disaster area.

In embodiments where a sensing device may be capable of detecting one or more different kinds of signals, the sensing device could be configured to automatically determine an appropriate baseline to use with each different signal. For example, if the sensing device receives heart activity information, it may automatically select a baseline heart activity signal. If, however, the device receives a signal corresponding to breathing activity information, it may automatically select a baseline breathing activity signal.

Figure 8:
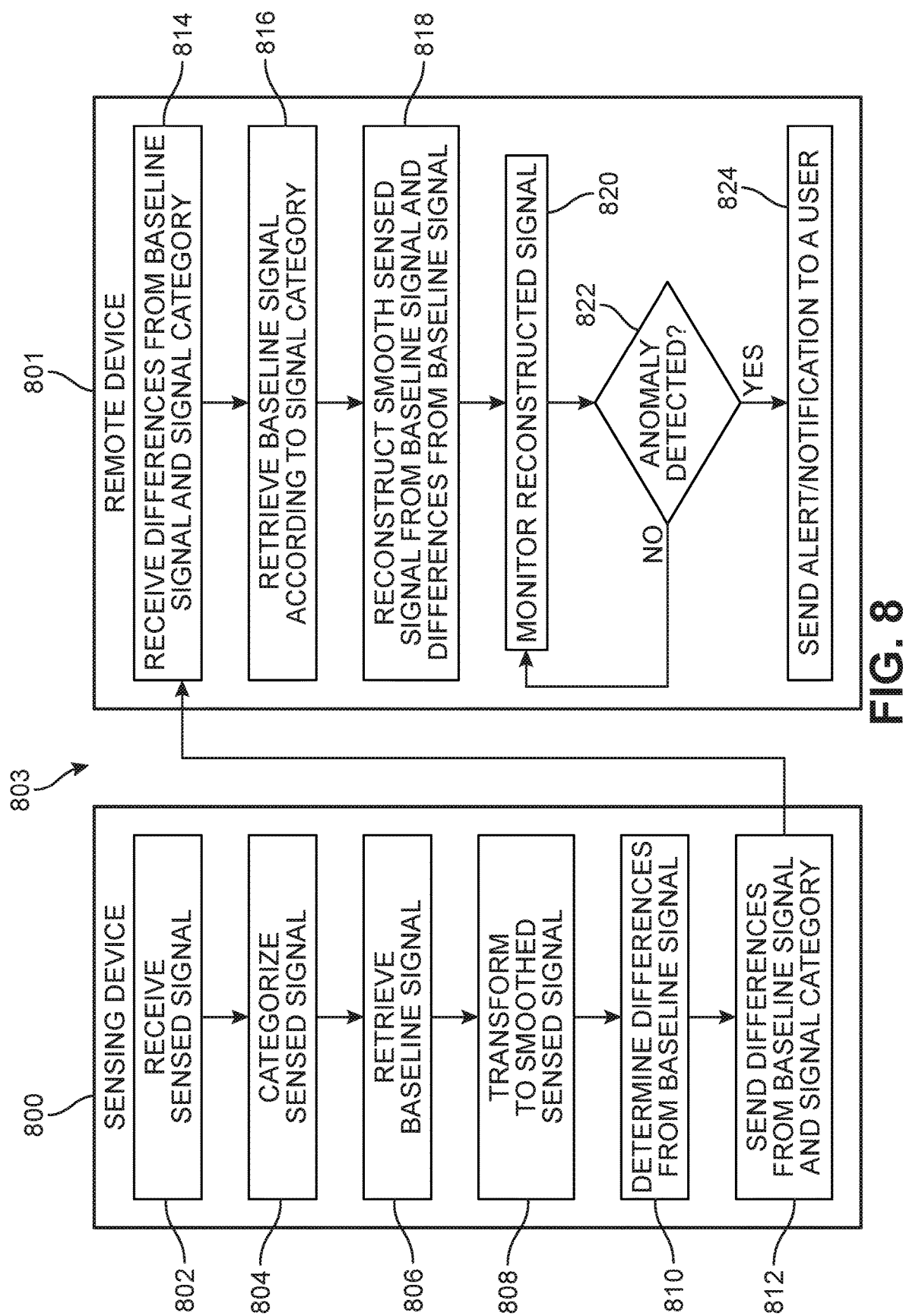
FIG. 8 is a schematic view of another process associated with a communication system, according to an embodiment.

FIG. 8 is an exemplary process 803 where a sensing device 800 automatically chooses an appropriate signal category and corresponding baseline signal. Starting in step 802, sensing device 202 may receive a sensed signal from one or more sensors. Next, in step 804, sensing device 202 may categorize (or classify) the signal. Categorization or classification could be accomplished using a machine learning algorithm to distinguish between different patterns of classes. Alternatively, algorithms could be used that search the signals for distinctive "signatures" or patterns that are unique to that particular kind of signal.

Once the signal has been categorized, an appropriate baseline signal may be retrieved in step 806. Following this, sensing device 202 may transform the sensed signal to a smoothed signal in step 808. Next, sensing device 202 may determine the differences between the smoothed sensed signal and the baseline signal in step 810. These differences may be sent to a remote device 801 in step 812. In addition, to sending the differences, sensing device 202 may also send the signal category that was determined in step 804.

Remote device 801 receives the differences between the smoothed sensed signal and the baseline signal along with the signal category in step 814. In step 816, remote device 801 retrieves the appropriate baseline signal (from multiple) according to the signal category. In step 818, remote device 801 reconstructs the smoothed sensed signal from the baseline signal and the differences received in step 814.

In step 820, remote device 801 may monitor the reconstructed signal. If an anomaly is detected in step 822, remote device 801 may send an alert or notification to a user in step 824. Here, the user could be an operator of the remote device, the person wearing the sensing device, or any other party. If no anomalies are detected in step 822, remove device 801 may return to step 818 to continue monitoring the signal.

Some sensing devices may include provisions for transmitting signal information based on the type of sensed information and its priority relative to other types of sensed information. For example, a sensing device may be configured to prioritize heart rate information over respiration information if the heart rate sensors are deemed more accurate than the respiration sensors. In that case, the sensing device may not only prioritize transmitting differences between the heart rate signal and the baseline heart rate signal over sending other information, but the sensing device may also store the full heart rate signal and attempt to transmit the full signal when connectivity is sufficient.

Figure 9:
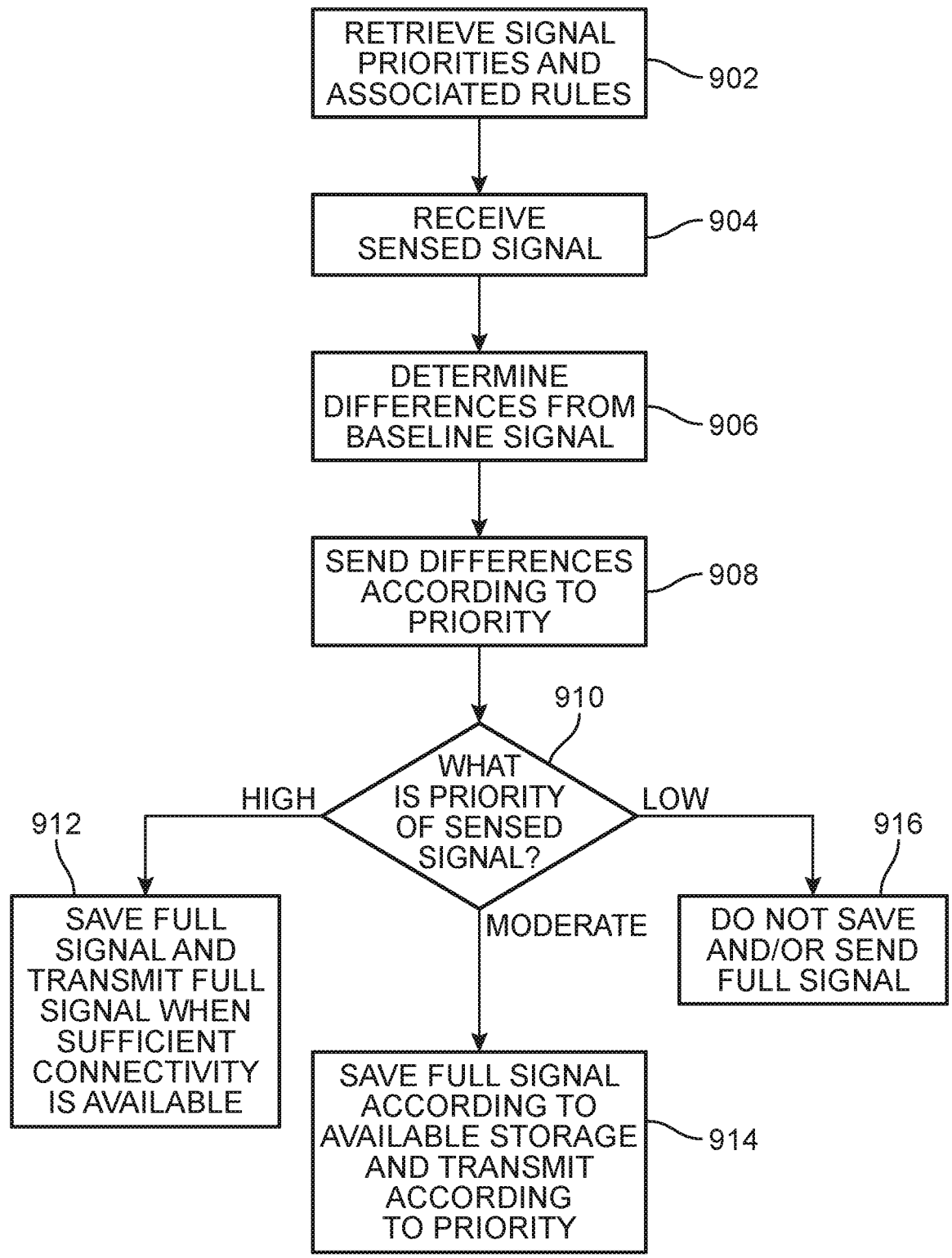
FIG. 9 is a schematic view of another process associated with a communication system, according to an embodiment.

FIG. 9 is a schematic view of a process for sending signal information according to priority levels and rules associated with the priority levels. Starting in step 902, a sensing device may retrieve signal priorities and associated rules for each type of signal. As an example, signal priorities could comprise three priority levels or types: a high priority, a moderate priority and a low priority. Alternatively, in some embodiments, each signal could be ranked so that the priority corresponds to the ranking. Next, in step 904, the sensing device may receive a sensed signal from a sensor (or multiple sensors). In step 906, the sensing device could determine the differences between the sensed signal and a baseline signal, as already described above. In step 908, the differences between the sensed signal and baseline signal could be sent to a remote device, or to other devices in a mesh network.

In step 910, the sensing device determines the priority of the sensed signal. If the sensed signal has a high priority, then the sensing device proceeds to step 912. In step 912, the sensing device may save the full signal (either the raw signal or the smoothed signal, for example). The sensing device may then wait to transmit the full signal when there is sufficient connectivity to transmit this higher quantity of data.

If the sensed signal has a moderate priority as determined in step 910, the sensing device proceeds to step 914. In step 914, the sensing device may save the full signal only if there is storage available. Specifically, in some cases, a smaller amount of storage may be allocated to moderate priority signals compared to high priority signals. The sensing device may then wait to transmit the full signal according to priority. For example, the sensing device may not transmit the full signal until all high priority signals have already been transmitted.

If the sensed signal has a low priority, as determined in step 910, the sensing device proceeds to step 916. In step 916, the sensing device may not save the full signal. Also, in some cases, the sensing device may not send the full signal. That is, for low priority signals, only the differences may be transmitted.

The processes and methods of the embodiments described in this detailed description and shown in the figures can be implemented using any kind of computing system having one or more central processing units (CPUs) and/or graphics processing units (GPUs). The processes and methods of the embodiments could also be implemented using special purpose circuitry such as an application specific integrated circuit (ASIC). The processes and methods of the embodiments may also be implemented on computing systems including read only memory (ROM) and/or random access memory (RAM), which may be connected to one or more processing units. Examples of computing systems and devices include, but are not limited to: servers, cellular phones, smart phones, tablet computers, notebook computers, e-book readers, laptop or desktop computers, all-in-one computers, as well as various kinds of digital media players.

The processes and methods of the embodiments can be stored as instructions and/or data on non-transitory computer-readable media. The non-transitory computer readable medium may include any suitable computer readable medium, such as a memory, such as RAM, ROM, flash memory, or any other type of memory known in the art. In some embodiments, the non-transitory computer readable medium may include, for example, an electronic storage device, a magnetic storage device, an optical storage device, an electromagnetic storage device, a semiconductor storage device, or any suitable combination of such devices. More specific examples of the non-transitory computer readable medium may include a portable computer diskette, a floppy disk, a hard disk, magnetic disks or tapes, a read-only memory (ROM), a random access memory (RAM), a static random access memory (SRAM), a portable compact disc read-only memory (CD-ROM), an erasable programmable read-only memory (EPROM or Flash memory), electrically erasable programmable read-only memories (EEPROM), a digital versatile disk (DVD and DVD-ROM), a memory stick, other kinds of solid state drives, and any suitable combination of these exemplary media. A non-transitory computer readable medium, as used herein, is not to be construed as being transitory signals, such as radio waves or other freely propagating electromagnetic waves, electromagnetic waves propagating through a waveguide or other transmission media (e.g., light pulses passing through a fiber-optic cable), or electrical signals transmitted through a wire.

Instructions stored on the non-transitory computer readable medium for carrying out operations of the present invention may be instruction-set-architecture (ISA) instructions, assembler instructions, machine instructions, machine dependent instructions, microcode, firmware instructions, configuration data for integrated circuitry, state-setting data, or source code or object code written in any of one or more programming languages, including an object oriented programming language such as Smalltalk, C++, or suitable language, and procedural programming languages, such as the "C" programming language or similar programming languages.

Aspects of the present disclosure are described in association with figures illustrating flowcharts and/or block diagrams of methods, apparatus (systems), and computing products. It will be understood that each block of the flowcharts and/or block diagrams can be implemented by computer readable instructions. The flowcharts and block diagrams in the figures illustrate the architecture, functionality, and operation of possible implementations of various disclosed embodiments. Accordingly, each block in the flowchart or block diagrams may represent a module, segment, or portion of instructions. In some implementations, the functions set forth in the figures and claims may occur in an alternative order than listed and/or illustrated.

The embodiments may utilize any kind of network for communication between separate computing systems. A network can comprise any combination of local area networks (LANs) and/or wide area networks (WANs), using both wired and wireless communication systems. A network may use various known communications technologies and/or protocols. Communication technologies can include, but are not limited to: Ethernet, 802.11, worldwide interoperability for microwave access (WiMAX), mobile broadband (such as CDMA, and LTE), digital subscriber line (DSL), cable internet access, satellite broadband, wireless ISP, fiber optic internet, as well as other wired and wireless technologies. Networking protocols used on a network may include transmission control protocol/Internet protocol (TCP/IP), multiprotocol label switching (MPLS), User Datagram Protocol (UDP), hypertext transport protocol (HTTP), hypertext transport protocol secure (HTTPS) and file transfer protocol (FTP) as well as other protocols.

Data exchanged over a network may be represented using technologies and/or formats including hypertext markup language (HTML), extensible markup language (XML), Atom, JavaScript Object Notation (JSON), YAML, as well as other data exchange formats. In addition, information transferred over a network can be encrypted using conventional encryption technologies such as secure sockets layer (SSL), transport layer security (TLS), and Internet Protocol security (Ipsec).

While various embodiments of the invention have been described, the description is intended to be exemplary, rather than limiting, and it will be apparent to those of ordinary skill in the art that many more embodiments and implementations are possible that are within the scope of the invention. Accordingly, the invention is not to be restricted except in light of the attached claims and their equivalents. Also, various modifications and changes may be made within the scope of the attached claims.

We claim:

1. A method of improving the efficiency of transmitting sensed information from a sensing device to a receiving device, comprising:
sensing a first sensed signal with a first sensor of the sensing device;
applying machine learning to the first sensed signal to classify the first sensed signal as belonging to a first signal category of a plurality of signal categories, wherein each signal category in the plurality of signal categories has a different signal pattern;
retrieving a first baseline signal corresponding to the first signal category;
transforming the first sensed signal into a first smoothed sensed signal;
determining differences between the first smoothed sensed signal and the first baseline signal;
sending at least some of the differences between the first smoothed sensed signal and the first baseline signal to the receiving device;
sensing a second sensed signal with a second sensor of the sensing device, wherein the second sensed signal is different from the first sensed signal;

applying machine learning to the second sensed signal to classify the second sensed signal as belonging to a second signal category of the plurality of signal categories;
retrieving a second baseline signal corresponding to the second signal category, wherein the second baseline signal is different than the first baseline signal;
transforming the second sensed signal into a second smoothed sensed signal;
determining differences between the second smoothed sensed signal and the second baseline signal;
sending at least some of the differences between the second smoothed sensed signal and the second baseline signal to the receiving device;
determining a first signal priority for the first sensed signal and determining a second signal priority for the second sensed signal; and
wherein after sending the at least some of the differences between the first smoothed sensed signal and the first baseline signal and sending the at least some of the differences between the second smoothed sensed signal and the second baseline signal, the method further comprises:
sending the first sensed signal to the remote device based on the first signal priority of the first sensed signal.

2. The method according to claim 1, wherein the method further comprises sending the second sensed signal to the remote device based on the second signal priority of the second sensed signal.

3. The method according to claim 2, wherein the order in which the first sensed signal and the second sensed signal are transmitted is determined by the first signal priority and the second signal priority.

4. The method according to claim 1, wherein the method further comprises not sending the second sensed signal to the remote device based on the second signal priority of the second sensed signal.

5. The method according to claim 1, wherein determining the differences between the first smoothed sensed signal and the first baseline signal includes using cross-correlation to determine lag between the first sensed signal and the first baseline signal.

6. The method according to claim 1, wherein sending at least some of the differences between the first smoothed sensed signal and the first baseline signal includes transmitting only differences that are substantially greater than zero.

7. The method according to claim 1, wherein the first baseline signal is stored prior to sensing the first sensed signal with the first sensor.

8. The method according to claim 7, wherein the method further includes sending the first signal category to the receiving device.

9. The method according to claim 1, the method further comprising:
receiving first data, the first data comprising differences between the first sensed signal and the first baseline signal;
receiving the first signal category associated with the first data;
retrieving the first baseline signal according to the received first signal category,
reconstructing a first new signal from the first baseline signal and the first data;
receiving second data, the second data comprising differences between the second sensed signal and the second baseline signal;
receiving the second signal category associated with the second data, wherein the second signal category is different than the first signal category;
retrieving the second baseline signal according to the received second signal category;
reconstructing a second new signal from the second baseline signal and the second data; and
after reconstructing the first baseline signal and the second baseline signal, receiving the first sensed signal.

10. The method according to claim 9, wherein the first sensed signal has a higher priority than the second sensed signal.

11. The method according to claim 9, wherein after receiving the first sensed signal the method further comprises receiving the second sensed signal.

12. The method according to claim 11, wherein the method further comprises monitoring the first new signal and detecting anomalous heart activity in the first new signal.

13. The method according to claim 12, wherein the method further comprises sending an alert to a user when the anomalous heart activity is detected.

14. A communication system for efficiently transmitting signals, comprising:
a device processor;
a non-transitory computer readable medium storing instructions that are executable by the device processor to:
sense a first sensed signal with a first sensor;
apply machine learning to the first sensed signal to classify the first sensed signal as belonging to a first signal category of a plurality of signal categories, wherein each signal category in the plurality of signal categories has a different signal pattern;
retrieve a first baseline signal corresponding to the first signal category;
transforming the first sensed signal into a first smoothed sensed signal;
determining differences between the first smoothed sensed signal and the first baseline signal;
send at least some of the differences between the first smoothed sensed signal and the first baseline signal to the receiving device;
sense a second sensed signal with a second sensor, wherein the second sensed signal is different from the first sensed signal;
apply machine learning to the second sensed signal to classify the second sensed signal as belonging to a second signal category of the plurality of signal categories;
retrieve a second baseline signal corresponding to the second signal category, wherein the second baseline signal is different than the first baseline signal;
transform the second sensed signal into a second smoothed sensed signal;
determine differences between the second smoothed sensed signal and the second baseline signal;
send at least some of the differences between the second smoothed sensed signal and the second baseline signal to the receiving device;
determine a first signal priority for the first sensed signal and determine a second signal priority for the second sensed signal; and
send the first sensed signal to the remote device based on the first signal priority of the first sensed signal after sending the at least some of the differences between the first smoothed sensed signal and the first baseline signal and sending the at least some of the differences between the second smoothed sensed signal and the second baseline signal.

15. The communication system according to claim 14, wherein the instructions are executable to send the second sensed signal to the remote device based on the second signal priority of the second sensed signal.

16. The communication system according to claim 15, wherein the order in which the first sensed signal and the second sensed signal are transmitted is determined by the first signal priority and the second signal priority.

17. The communication system according to claim 14, wherein the first sensor is an optical blood flow sensor.

18. The communication system according to claim 14, wherein the first sensor is an oximetry sensor.

19. The communication system according to claim 14, wherein the first sensor is a respiration sensor.

20. The communication system according to claim 14, wherein the first sensed signal is an electrical signal associated with heart activity.

* * * * *